United States Patent [19]

Fontanella et al.

[11] 3,985,811

[45] Oct. 12, 1976

[54] 5-CHLORO-2-HYDROXYMETHYL BENZHYDROL

[75] Inventors: Luigi Fontanella; Luigi Mariani, both of Milan, Italy

[73] Assignee: Gruppo Lepetit S.p.A., Milan, Italy

[22] Filed: May 23, 1973

[21] Appl. No.: 363,226

[52] U.S. Cl. ............................ 260/618 B; 260/602; 260/611 A; 260/469; 260/471 C; 260/471 R; 424/343
[51] Int. Cl.$^2$ ........................................ C07C 33/02
[58] Field of Search ................................ 260/618 B

[56] References Cited
OTHER PUBLICATIONS

Pernot et al., "Bull. Soc. Chim. de France," p. 322, (1953).
Bloniquist et al., "Chemical Abstracts," vol. 57, pp. 7180–7182, (1962).
Pernot et al., "Bull. Soc. Chim. France," p. 321, (1953).

*Primary Examiner*—Nicholas S. Rizzo
*Assistant Examiner*—D. B. Springer
*Attorney, Agent, or Firm*—Theodore Post; C. Kenneth Bjosh

[57] ABSTRACT

Pharmacologically active diphenylmethane derivatives of formula (I)

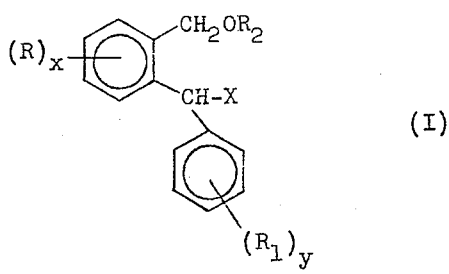

wherein: R is halo, nitro or lower alkoxy; $R_1$ is hydrogen, halo, nitro, lower alkyl or lower alkoxy; $R_2$ is hydrogen, lower acyl, carbamyl or substituted carbamyl; X is an —$OR_3$ or —$NHR_4$ group wherein $R_3$ is hydrogen, lower alkyl, phenyl, substituted phenyl, phenyl-lower alkyl, acyl, carbamyl or substituted carbamyl; $R_4$ is hydrogen, lower alkyl or lower acyl; and x and y are integers from zero to two, provided that the sum of x and y is at least one. The compounds are prepared by hydrogenation of an o-benzoylbenzoic acid of formula (II) to the corresponding diol of formula (III) according to the following scheme:

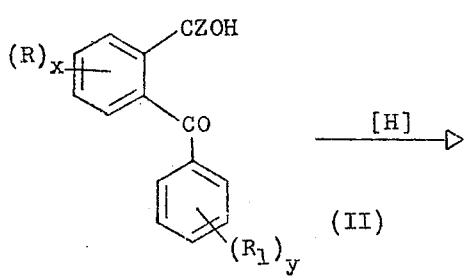

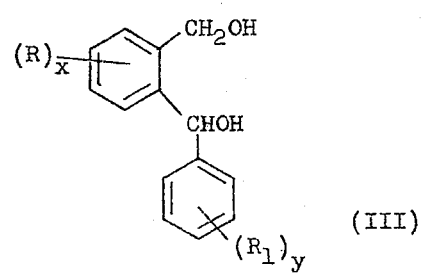

wherein R, $R_1$, x and y have the same meaning given above and Z is O or $H_2$. As hydrogenating agents, a hydride or mixed metal hydrides are used. The diols of formula (III) may be subsequently coverted to other inventive compounds of formula (I) by simple chemical operations. The compounds have CNS depressant activity.

1 Claim, No Drawings

5-CHLORO-2-HYDROXYMETHYL BENZHYDROL

BACKGROUND OF THE INVENTION

The 2-hydroxymethyl-benzhydrol is known; Pernot et al., Bull. Soc. Chim. France, 1953, 321. 2-Aminomethyl-benzhydrols are described by K. Freter et al. in Canadian Journal of Chemistry 48, 1670 (1970). However, no C.N.S. depressant activity is disclosed for these compounds by either publication.

SUMMARY OF THE INVENTION

The present invention relates to pharmacologically active diphenylmethane derivatives represented by formula (I)

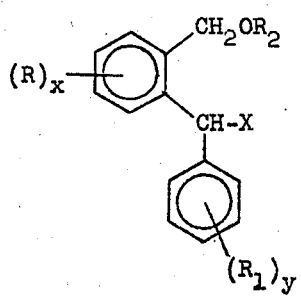

(I)

wherein R represents halogen, nitro or lower alkoxy; $R_1$ represents hydrogen, halo, nitro, lower alkyl or lower alkoxy; $R_2$ represents hydrogen, lower acyl, carbamyl or substituted carbamyl; X represents $-OR_3$ or $-NHR_4$ wherein $R_3$ represents hydrogen, lower alkyl, phenyl, substituted phenyl, phenyl lower alkyl, lower acyl, carbamyl or substituted carbamyl; $R_4$ represents hydrogen, lower alkyl or lower acyl; and $x$ and $y$ each represents an integer from zero to two, provided that the sum of $x$ and $y$ is at least one.

In the specification and claims, the term "lower alkyl" as such and in compound terms designates alkyl groups having from 1, to 2, to 3, to 4, to 5, to 6 carbon atoms and their unsaturated derivatives having a double or triple bond. The term "substituted phenyl" refers to phenyl groups which carry halo, nitro, lower alkyl, hydroxy or dimethylsulfamoyl substituent groups. The term "lower acyl" identifies groups derived from lower aliphatic carboxylic acids having from 2 to 6 carbon atoms. "Substituted carbamyl" identifies carbamyl having lower alkyl or phenyl substitution; and "halo" identifies fluoro, chloro or bromo.

The following parts of the specification further describe the invention and the manner and process of making and using it to enable the art skilled to make and use the same and set forth the best mode contemplated by the inventors of carrying out the invention.

DESCRIPTION OF THE PREFERRED EMBODIMENTS

The process for the preparation of the starting compounds on which the compounds of the invention are based comprises the hydrogenation of an o-benzoyl benzoic acid of formula (II) to the corresponding diols of formula (III) pursuant to the following scheme:

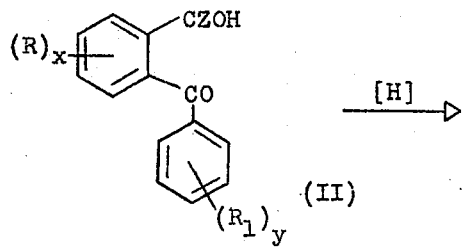

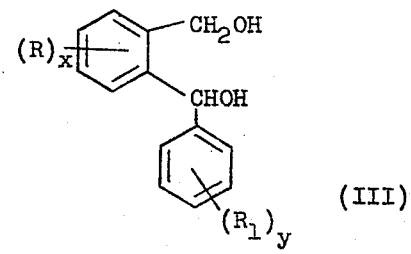

wherein R, $R_1$, $x$ and $y$ have the same meaning as given before and Z represents O or $H_2$. As hydrogenating agents, a hydride and preferably a mixed metal hydride is used. These include, for example, boron hydride, light metal hydrides, i.e., alkali metal and alkaline-earth metal hydrides, and mixed metal hydrides such as alkali metal borohydrides and alkali metal aluminum hydrides. Of these hydrides, lithium aluminum hydride is preferred. In the preparation of the starting compounds, a compound of formula (II) is added with stirring to, for example, a suspension of lithium aluminum hydride in an inert organic solvent such as, for instance, ethyl ether, tetrahydrofuran, dioxane, benzene or their mixtures. The amount of hydride employed is advantageously in substantial excess over the stoichiometric amount required for the reaction. The reaction temperature is maintained within a range of about 0° C. to room temperature. The reaction time may vary from one hour to several hours depending on the reactivity of the substrate (II). The recovery of hydrogenated product (III) after decomposition of the reaction complex by adding aqueous 20 percent ammonium chloride, is carried out according to usual technical procedures which include evaporation of the organic layer and crystallization of the crude product obtained from a suitable solvent.

The diols of formula (III) are subsequently converted to other inventive compounds of formula (I) by other chemical operations. For instance, reaction of a diol of formula (III) with an excess of isocyanic acid or an isocyanate according to procedures generally employed for such reactions gives the corresponding compounds of formula (I) wherein $R_2$ and $R_3$ represent carbamyl or a substituted carbamyl group.

Reaction with an acid anhydride or an acid halide of a diol of formula (III) in the presence of an acid acceptor gives a mixture of mono- and di-acyl derivatives which are readily separated by fractional crystallization. The proportions of mono- and di-acyl compound vary according to the reaction conditions. Elevated temperatures or prolonged reaction time favor the formation of the diacyl derivatives.

The mono-acyl derivatives are compounds of formula (III) wherein the primary alcoholic function is acylated and, therefore, they may also be used as intermediates for preparing the compound of formula (I) wherein X is different from hydroxy. For this purpose, a compound represented by formula (IV)

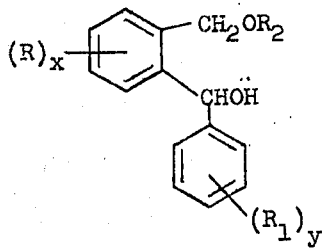

(IV)

wherein R, $R_1$, x and y have the same meaning as given before and $R_2$ is an acyl moiety derived from a lower aliphatic acid, are advantageously employed. In this connection, the free hydroxyl group may be readily converted into a halo group by reaction with phosphorus or thionyl halide and the obtained halo-compound may in turn be transformed into the corresponding amino derivative through nucleophilic displacement with a selected amine. A subsequent alkaline hydrolysis gives a compound represented by formula (I) wherein $R_2$ is hydrogen and X is $NHR_4$ wherein $R_4$ is hydrogen or lower alkyl, which compound may in turn be converted to another representative compound of the invention by a known chemical transformation of the hydroxyl and/or amino moiety. Alkylation, acylation and carbamylation are the most common operations which may be effected on such substrates.

When a lower alkanol solution of a halo-compound as described above is heated with ammonia under superatmospheric pressure, nucleophilic displacement of the halo group by an amino group is accompanied by migration of the lower aliphatic acyl group from the alcoholic moiety to the amino function giving a compound of formula (I) wherein $R_2$ is hydrogen and $R_4$ is lower acyl.

Mineral acid hydrolysis of one of the last mentioned compounds leads to a derivative of formula (I) wherein both $R_2$ and $R_4$ are hydrogen. Of course, in this case too, the two resulting functional groups may be further transformed through acylation, alkylation or carbamylation.

The starting o-benzoyl-benzoic acid and o-hydroxymethyl benzophenones may be prepared by known literature methods such as the Friedel-Crafts reaction of phthalic anhydrides with benzene derivatives and ring opening of the phthalide compound by means of a predetermined aryl magnesium halide.

EXAMPLE 1

5-Chloro-2-hydroxymethyl-benzhydrol

A suspension of 120 g. of 2-benzoyl-4-chlorobenzoic acid in 900 ml. of anhydrous ethyl ether is added dropwise to 41 g. $LiAlH_4$ suspended in 700 ml. of anhydrous ethyl ether with stirring at about 0° C. When the addition is completed, the mixture is stirred for 4 hours at room temperature and the reaction complex is decomposed by adding 125 ml. of 20% ammonium chloride with stirring. The inorganic precipitate is filtered off and washed with ethyl ether. The ether solutions are combined, dried over sodium sulfate and evaporated to dryness. The oily residue is triturated with light petroleum and the solid obtained is crystallized from diisopropyl ether. M.p. 102°–107° C. Yield 105 g.

EXAMPLE 2

5-Chloro-2-methylcarbamyloxymethyl-benzhydrol methylcarbamate

In a Parr bomb, 2 g. of the compound of Example 1 is heated for 7 hours at 80°–90° C. with 2 g. of methyl isocyanate and 6 ml. of pyridine. After cooling, the reaction mixture is boiled in methanol for 5 minutes and the solvent is distilled off. The crude residue is triturated with acidic water, and after decantation is dissolved in anhydrous ethyl ether. Concentration of the ether solution gives a product that after crystallization from diisopropyl ether melts at 128°–131° C. Yield 2 g.

EXAMPLE 3

5-Chloro-2-phenylcarbamyloxymethyl-benzhydrol phenylcarbamate

A mixture of 2 g. of the compound of Example 1, 2 ml. of phenyl isocyanate and 4 ml. of pyridine are refluxed for 45 minutes. The reaction mixture is then boiled for 5 minutes with methanol and the solvent is distilled off. The crude solid obtained is triturated with acidic water, then crystallized from ethanol. M.p. 192°–196° C. Yield 2.5 g.

EXAMPLE 4

2-Acetoxymethyl-5-chloro-benzhydrol

To a solution of 97 g. of the compound of Example 1 in 550 ml. of benzene, 75 ml. of acetic anhydride is added and the mixture is gently refluxed for 3 hours. The cooled solution is washed with aqueous sodium bicarbonate, then with water. The organic phase is dried over sodium sulphate and evaporated to dryness. The residue, after trituration with light petroleum, is crystallized from a mixture of ethyl ether and benzol. M.p. 86°–88° C. Yield 60 g.

EXAMPLE 5

2-Acetoxymethyl-5-chloro-α-(phenyl)benzyl bromide

To a solution of 45 g. of 2-acetoxymethyl-5-chlorobenzhydrol in 270 ml. of ethyl ether, 13.7 g. of phosphorus tribromide in 45 ml. ethyl ether is added and the solution is stirred for 3 hours at room temperature. The organic solution is successively washed with a sodium bicarbonate solution and with water. After drying over sodium sulfate and evaporation of the solvent, 43.1 grams of the crude title compound is obtained which may be used for further reaction steps. B.p. 175°–180° C. 0.5 mm Hg.

EXAMPLE 6

4-Chloro-2-[α-(methylamino)benzyl]benzyl alcohol

To a solution of 24 g. of the compound of Example 5 in 400 ml. of anhydrous benzene, 53 ml. of a 5.1% solution of methylamine in benzene is added and the mixture is maintained at room temperature for 24 hours. The solid precipitate is filtered off and the benzene solution is evaporated to dryness. The residue is then transformed into the corresponding hydrochloric acid salt by addition of methyl ether saturated with hydrogen chloride. The resulting product is used as such for the subsequent hydrolysis step.

7.5 Grams of the latter compound is dissolved at room temperature in a mixture of 160 ml. of ethanol, 24 ml. of 11% potassium hydroxide and 50 ml. of water. After 12 hours, ethanol is distilled off at about 50° C. and the residue is extracted with ethyl ether. The organic layer is then evaporated to dryness to give 2.3 g. of product which after crystallization from diisopropyl ether gives the titular product. M.p. 117°–118° C.

EXAMPLES 7 – 9

By following the procedure of Exampl 6 but substituting an equivalent amount of Example propylamine or butylamine for methylamine, the following compounds are obtained:

7. 4-Chloro-2-[α-(ethylamino)benzyl]benzyl alcohol. B.p. 190°–195° C. 0.5 mm Hg.
8. 4-Chloro-2-[α-(propylamino)benzyl]benzyl alcohol hydrochloride, m.p. 225°–227° C.
9. 4-Chloro-2-[α-(butylamino)benzyl]benzyl alcohol. B.p. 190°–195° C. 0.4 mm Hg.

EXAMPLE 10

4-Chloro-2-[α-(acetamido)benzyl]benzyl alcohol

In a Parr bomb containing 47 g. of the compound of Example 5 in 200 ml. of ethanol, dry ammonia is introduced to a pressure of 5 atmospheres. After heating for 4 hours at 100° C., the resulting solution is evaporated. The oily residue is successively washed with light petroleum and diisopropyl ether, then it is taken up in a mixture of water and ethyl ether to give a solid which is used as such for the subsequent hydrolysis. Yield 16 g. A sample of the titular product crystallized from a mixture of ethyl ether and light petroleum melts at 131°–135° C.

EXAMPLE 11

4-Chloro-2-[α-(amino)benzyl]benzyl alcohol

Twelve g. of the compound of Example 10 is refluxed for two hours in 300 ml. of 10% hydrochloric acid. The cooled solution is washed with ethyl ether, then made alkaline with sodium hydroxide. After extraction with ethyl ether and evaporation of the organic phase, an oily residue is obtained which is triturated with isopropyl ether. The solid titular product so obtained melts at 113°–115° C. Yield 9 g. Its hydrochloride, obtained by addition of dry HCl to ethyl ether, melts at 194°–197° C. when crystallized from a mixture of ethyl alcohol and ethyl ether.

EXAMPLE 12

4',5-Dichloro-2-hydroxymethyl-benzyhydrol

To a suspension of 12 g. of LiAlH$_4$ in 100 ml. of ethyl ether, 24 g. of 4',5-dichloro-2-hydroxymethyl-benzophenone is added at 0°–5° C. The mixture is stirred for two hours at room temperature, then 36 ml. of water is added with cooling to about 5° C. The inorganic precipitate is filtered off and the organic solution is evaporated in vacuo. The residue is purified by column chromatography through silica gel by eluting with benzol: ethyl ether 95:5. Yield 14 g. of the titular product. M.p. 84°–86° C. (crystallized from isopropyl ether).

EXAMPLE 13

4',5-Dichloro-2-hydroxymethylbenzophenone

Magnesium turnings (2.5 g.) are suspended in 20 ml. of ethyl ether and 19 g. of 4-chlorobromobenzol in 35 ml. of ethyl ether is added to the mixture which is then refluxed for two hours. After cooling to room temperature, 16.8 g. of 6-chlorophthalide in 100 ml. of anhydrous benzene is added and the solution is heated at 50°–60° C. for about 1 hour. The reaction mixture is cooled and stirred with 50 ml. of aqueous 20% ammonium chloride. The organic phase is separated and washed with aqueous sodium bicarbonate, then with water. Evaporation yields 24 g. of crude titular product which is hydrogenated according to the procedure of the foregoing example to give the corresponding benzhydrol.

EXAMPLES 14–20

By reducing under conditions as described in Example 12, the corresponding benzophenones prepared according to the procedure of Example 13 give the following benzhydrols:

14. 2',5-Dichloro-2-hydroxymethylbenzhydrol M.p. 91°–93° C.
15. 3',5-Dichloro-2-hydroxymethylbenzhydrol M.p. 115°–117° C.
16. 2'-Methyl-5-chloro-2-hydroxymethylbenzhydrol M.p. 112°–114° C.
17. 3'-Methyl-5-chloro-2-hydroxymethylbenzhydrol M.p. 75°–77° C.
18. 4'-Methyl-5-chloro-2-hydroxymethylbenzhydrol B.p. 220° C. 0.8 mm Hg
19. 2'-Chloro-5-fluoro-2-hydroxymethylbenzhydrol M.p. 95°–97° C.
20. 2'-Fluoro-5-chloro-2-hydroxymethylbenzhydrol M.p. 109°–111° C.

Pursuant to procedures described in previous examples, other compounds of formula (I) may be prepared wherein the given symbols have the following meanings:

| R | R$_1$ | R$_2$ | X |
|---|---|---|---|
| 5-NO$_2$ | 2-CH$_3$ | H | OC$_6$H$_5$ |
| 5-Cl | 3-Cl | H | OC$_3$H$_7$ |
| 4,5-CH$_3$O | H | H | OH |
| 5-(CH$_3$)$_2$NSO$_2$ | H | H | OH |
| 5-Cl | 3-NO$_2$ | H | OH |
| 5-Cl | 4-Cl | COCH$_2$CH$_3$ | OCOCH$_2$CH$_3$ |
| 4-OC$_2$H$_5$ | 4,5-Cl | H | OH |
| 5-Cl | H | H | OCOOCH$_2$CH$_2$OH |
| 4-Cl | H | COOCH$_2$CH$_2$OH | OCOOCH$_2$-CH$_2$-OH |
| 5-F | 3-CH$_3$ | COC$_4$H$_9$ | NHC$_4$H$_9$ |
| 4-Cl | H | H | -NH-CH$_2$-CH=CH$_2$ |
| 5-Cl | H | H | -NH-CH$_2$-C≡CH |
| 5-Cl | 4-Br | H | NH$_2$ |
| 6-NO$_2$ | 2-CH$_3$ | H | OH |
| 5-CH$_3$ | 2-CH$_3$ | H | OH |
| 4-NO$_2$ | 4-CH$_3$ | H | OH |
| 6-Cl | 2,5-CH$_3$ | H | OH |
| 4-Cl | 2-F | COOC$_2$H$_5$ | OCOOC$_2$H$_5$ |

The inventive compounds are useful as CNS depressants. They display a remarkable myorelaxing, sedative and hypnotic effect in laboratory animals.

In laboratory experiments, individual doses of representative inventive compounds varying from about 30 to about 60 mg/kg i.p. were administered to mice and proved to be effective on the Irwing test parameters which are correlated with the above mentioned effects, i.e., body tone, decrease of spontaneous activity, impairment of motor coordination and righting reflex. For example, the compound of Example 1 is active on the above parameters in the monkey at 0.5 mg/kg i.p.

The new compounds have a low toxicity, the LD$_{50}$ in mice being generally higher than 500 mg/kg i.p.

What is claimed is:

1. The compound 5-chloro-2-hydroxymethyl-benzhydrol.

* * * * *

UNITED STATES PATENT AND TRADEMARK OFFICE
CERTIFICATE OF CORRECTION

PATENT NO. : 3,985,811
DATED : October 12, 1976
INVENTOR(S) : Luigi Fontanella, Luigi Mariani It is certified that error appears in the above-identified patent and that said Letters Patent are hereby corrected as shown below:

Title page, item [30] has been omitted, it should read as follows:

Foreign Application Priority Data
June 23, 1972   Italy    .... 26111 A/72

Title page, second column, line following III formula, "coverted" should read --converted--.

Column 1, line 9, "depressent" should read --depressant--.

Column 5, line 13, "Exampl" should read --Example--.

Column 5, line 14, "Example" should read --ethylamine,--.

Signed and Sealed this

Seventh Day of June 1977

[SEAL]

Attest:

RUTH C. MASON
*Attesting Officer*

C. MARSHALL DANN
*Commissioner of Patents and Trademarks*